(12) United States Patent
Pereira et al.

(10) Patent No.: US 8,515,687 B2
(45) Date of Patent: Aug. 20, 2013

(54) DEGRADATION DETECTION SYSTEM FOR A HOSE ASSEMBLY

(75) Inventors: Luis R. Pereira, Menomonee Falls, WI (US); B. Thomas Pier, Milwaukee, WI (US); Atul S. Bhadkamkar, Bayside, WI (US); Vehbi C. Gungor, Istanbul (TR); Carlos H. Rentel, Hanover, NH (US); Jason D. Stark, Maumee, OH (US); Scott A. Smith, Toledo, OH (US)

(73) Assignee: Eaton Corporation, Cleveland, OH (US)

( * ) Notice: Subject to any disclaimer, the term of this patent is extended or adjusted under 35 U.S.C. 154(b) by 680 days.

(21) Appl. No.: 12/579,448

(22) Filed: Oct. 15, 2009

(65) Prior Publication Data
US 2010/0174495 A1   Jul. 8, 2010

Related U.S. Application Data

(60) Provisional application No. 61/142,752, filed on Jan. 6, 2009.

(51) Int. Cl.
*G01B 21/32* (2006.01)
*G01B 21/30* (2006.01)
*G06F 3/01* (2006.01)
*G06F 3/03* (2006.01)

(52) U.S. Cl.
USPC ............... 702/34; 702/33; 702/179; 702/182

(58) Field of Classification Search
USPC ............. 702/34, 36, 45, 47, 51, 82, 179, 182, 702/188, 189; 73/146; 138/104; 380/270; 422/518
See application file for complete search history.

(56) References Cited

U.S. PATENT DOCUMENTS

| | | | |
|---|---|---|---|
| 6,551,558 B1 * | 4/2003 | Mann et al. | 422/518 |
| 7,609,838 B2 * | 10/2009 | Westhoff et al. | 380/270 |
| 7,752,904 B2 * | 7/2010 | Krutz et al. | 73/146 |
| 2004/0065377 A1 * | 4/2004 | Whiteley | 138/104 |
| 2005/0220306 A1 | 10/2005 | Westhoff et al. | |
| 2006/0185878 A1 * | 8/2006 | Soffer | 174/50 |
| 2006/0196252 A1 | 9/2006 | Deckard | |
| 2007/0131035 A1 | 6/2007 | Krutz et al. | |
| 2007/0156320 A1 | 7/2007 | Breed et al. | |
| 2008/0258878 A1 | 10/2008 | Dietrich et al. | |

FOREIGN PATENT DOCUMENTS

| | | |
|---|---|---|
| EP | 0695902 B1 | 2/1996 |
| FR | 2847342 A1 | 5/2004 |
| JP | 2007163324 A | 6/2007 |
| WO | 0058752 A1 | 10/2000 |
| WO | 2006066176 A2 | 6/2006 |
| WO | 2006071477 A1 | 7/2006 |
| WO | 2008054806 A2 | 5/2008 |

* cited by examiner

*Primary Examiner* — Marc Armand
*Assistant Examiner* — Felix Suarez
(74) *Attorney, Agent, or Firm* — Quinn Law Group, PLLC

(57) ABSTRACT

A hose fault detection system includes a hose assembly including a hose having first and second conductive layers. The hose assembly has an electrical characteristic. A fault detector is in electrical communication with the first and second conductive layers. The fault detector includes an indicator operatively connected to the hose assembly. A method for monitoring the structural integrity of a hose assembly includes providing a fault detection system having a hose assembly including a hose having a first conductive layer and a second conductive layer. The hose assembly has an electrical characteristic. The electrical characteristic of the hose assembly is compared to a threshold value. A visual indicator in operative communication with the hose assembly is illuminated when the electrical characteristic goes beyond the threshold value.

10 Claims, 14 Drawing Sheets

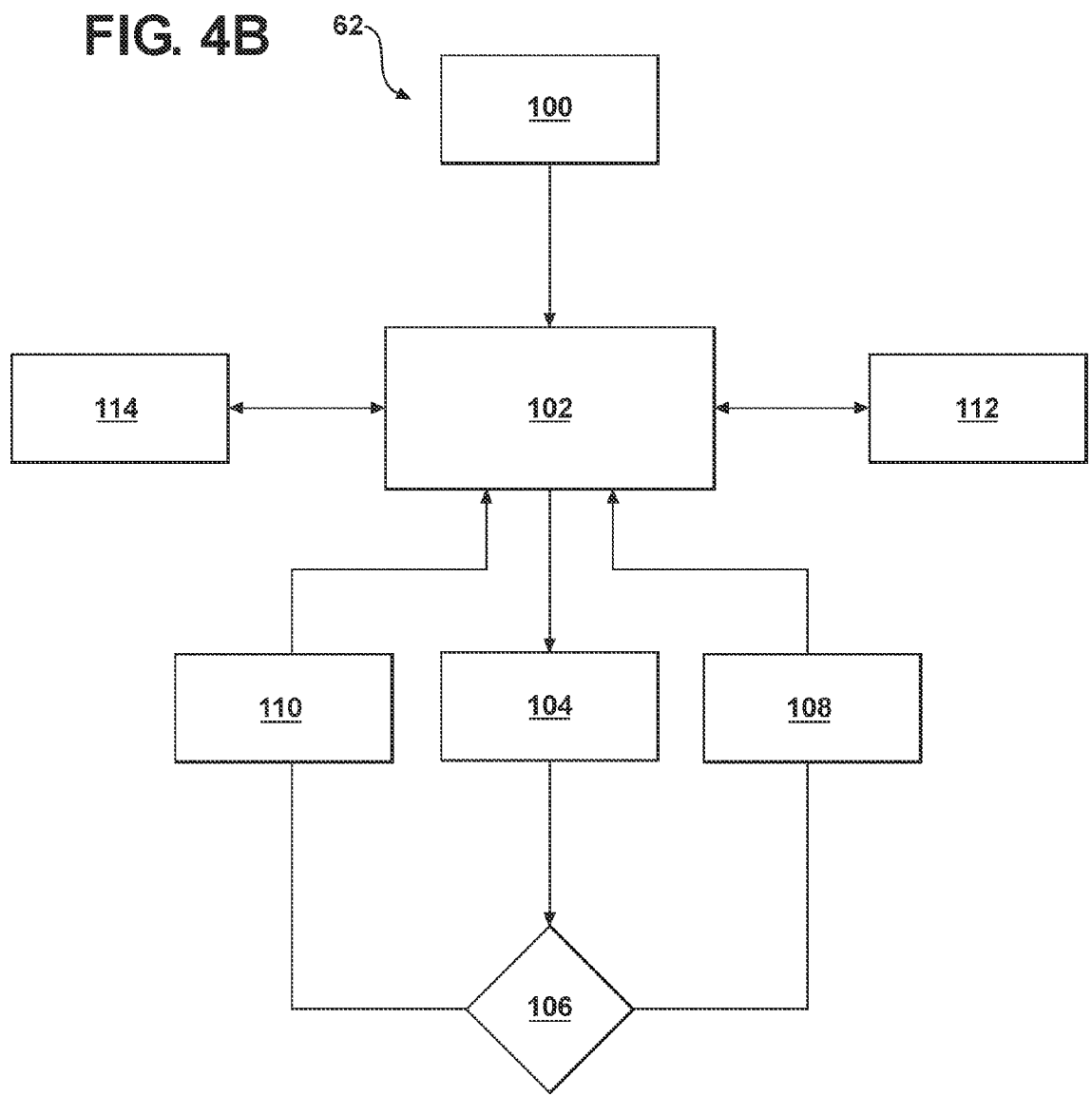

DEGRADATION DETECTION SYSTEM FOR A HOSE ASSEMBLY

CROSS-REFERENCE TO RELATED APPLICATIONS

This application claims the benefit of U.S. Provisional Application 61/142,752, filed Jan. 6, 2009, and which is hereby incorporated by reference in its entirety.

TECHNICAL FIELD

The present invention relates to a system for detecting degradation of a hose assembly.

BACKGROUND OF THE INVENTION

High pressure reinforced hydraulic hose is typically used on a variety of fluid power operated machines, such as earthmoving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube.

Many applications require hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance.

To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

SUMMARY OF THE INVENTION

An aspect of the present disclosure relates to a hose fault detection system. The hose fault detection system includes a hose assembly including a hose having a first conductive layer and a second conductive layer. The hose assembly has an electrical characteristic. A fault detector is in electrical communication with the first and second conductive layers. The fault detector includes at least one visual indicator operatively connected to the hose assembly.

In another aspect of the invention, an RFID-based hose fault detection system includes a plurality of hose assemblies, a plurality of RFID tag systems, a life-sensing hose detection mechanism, an algorithm, at least one reader, and at least one user interface. The hose assemblies each include a hose with an electrical characteristic. The RFID tag systems are in communication with the hose assemblies. The user interface is configured to display the electrical characteristic of the hose of the hose assembly.

In yet another aspect of the invention, a monitoring and failure detection system includes at least one hose assembly, at least one sensor node, and at least one aggregator node. The hose assembly includes a hose having an electrical characteristic. The sensor node has a plurality of sensors that are operatively attached to the hose assembly and are configured to monitor the electrical characteristic. The aggregator node is in operative communication with the sensor node. The sensor node is configured to provide data pertaining to the electrical characteristic to the aggregator node. The aggregator node is configured to analyze the data and provide information of the hose assembly to a system operator via a user interface.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

The above features and advantages and other features and advantages of the present invention are readily apparent from the following detailed description of the best modes for carrying out the invention when taken in connection with the accompanying drawings.

BRIEF DESCRIPTION OF THE DRAWINGS

Referring now to the figures, which are exemplary embodiments and wherein like elements are numbered alike:

FIG. 4B is a schematic illustration of an algorithm of the microcontroller device of FIG. 4A that is used to read and record electrical resistance values of the conductive layers of the hose in a memory;\

DESCRIPTION OF THE PREFERRED EMBODIMENTS

Figure 1:
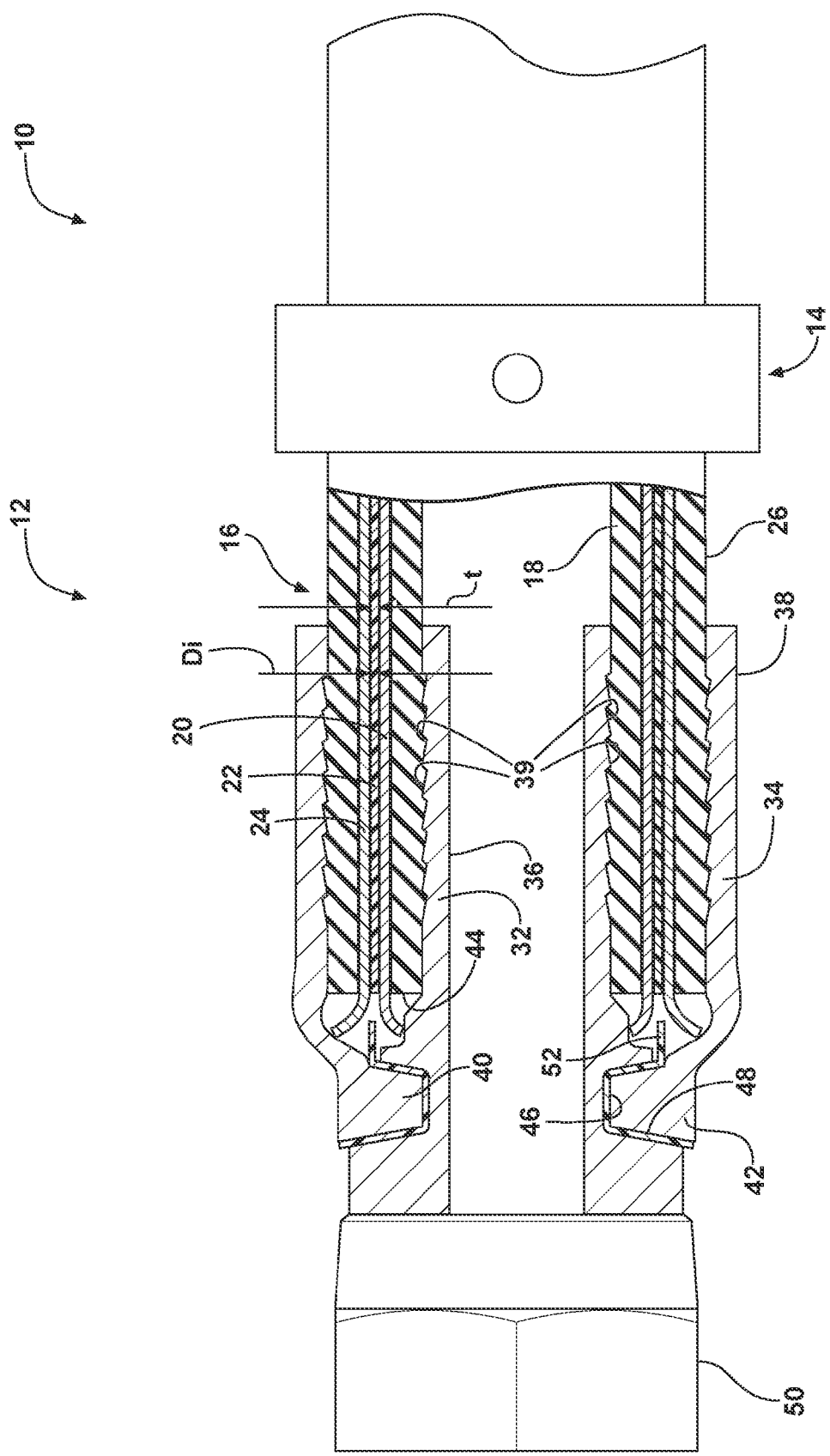
FIG. 1 is a partial cross-sectional view of an exemplary hose assembly employing a fault detector having exemplary features of aspects in accordance with the principles of the present disclosure.

Referring to the drawings, wherein like reference numbers refer to like components, FIG. 1 shows a hose fault detection system, generally designated at 10. The hose fault detection system 10 includes a hose assembly, generally designated 12, and a fault detector 14 in electrical communication with the hose assembly 12.

The hose assembly 12 includes a hose, generally designated 16, having a multi-layer construction. In the subject embodiment, the hose 16 is generally flexible and includes an inner tube 18 made from a polymeric material, such as rubber or plastic, or another material depending on the requirements of the particular application, a first conductive layer 20, an intermediate layer 22, a second conductive layer 24 and an outer cover 26. The first and second conductive layers 20, 24 and the intermediate layer 22 define an electrical characteristic of the hose assembly 12, such as capacitance, inductance and/or resistance (impedance).

In the subject embodiment, the first conductive layer 20 overlays the inner tube 18 and the intermediate layer 22 overlays the first conductive layer 20. The second conductive layer 24 overlays the intermediate layer 22. The first and second conductive layers 20, 24 may be configured as reinforcing layers. The outer cover 26 may overlay the second conductive layer 24, and may include, for example, an extruded layer of rubber or plastic (not shown). The outer cover 26 may itself include a reinforcing layer (not shown).

The intermediate layer 22 operates to at least partially insulate electrically the first and second conductive layers 20, 24 from one another. The intermediate layer 22 may have any of a variety of constructions. For example, the intermediate layer 22 may consist of a single layer of an electrically resistive material. The intermediate layer 22 may also consist of multiple layers, wherein at least one of the layers exhibits electrical insulating properties. Certain composite materials may also be employed in the intermediate layer 22, such as a woven fabric bonded to a polymeric material. Composite materials having various other constructions may also be utilized. Composite materials may also be used in combination with other materials to form the intermediate layer 22.

The first and second conductive layers 20, 24 generally extend the entire length and span the entire circumference of the hose. This is generally the case when the conductive layers also function as a reinforcement layer. The intermediate layer 22 may also extend over the entire length and circumference of the hose. There may be instances, however, where at least one of the first and second conductive layers 20, 24 extend only over a portion of the length of the hose and/or a portion the circumference of the hose. In those instances, the intermediate layer 22 may also be configured to generally extend over the region of the hose that includes only the partial conductive layers 20, 24. The partial intermediate layer 22 may be positioned within the hose so as to separate the first and second conductive layers 20, 24 from one another.

Figure 2:
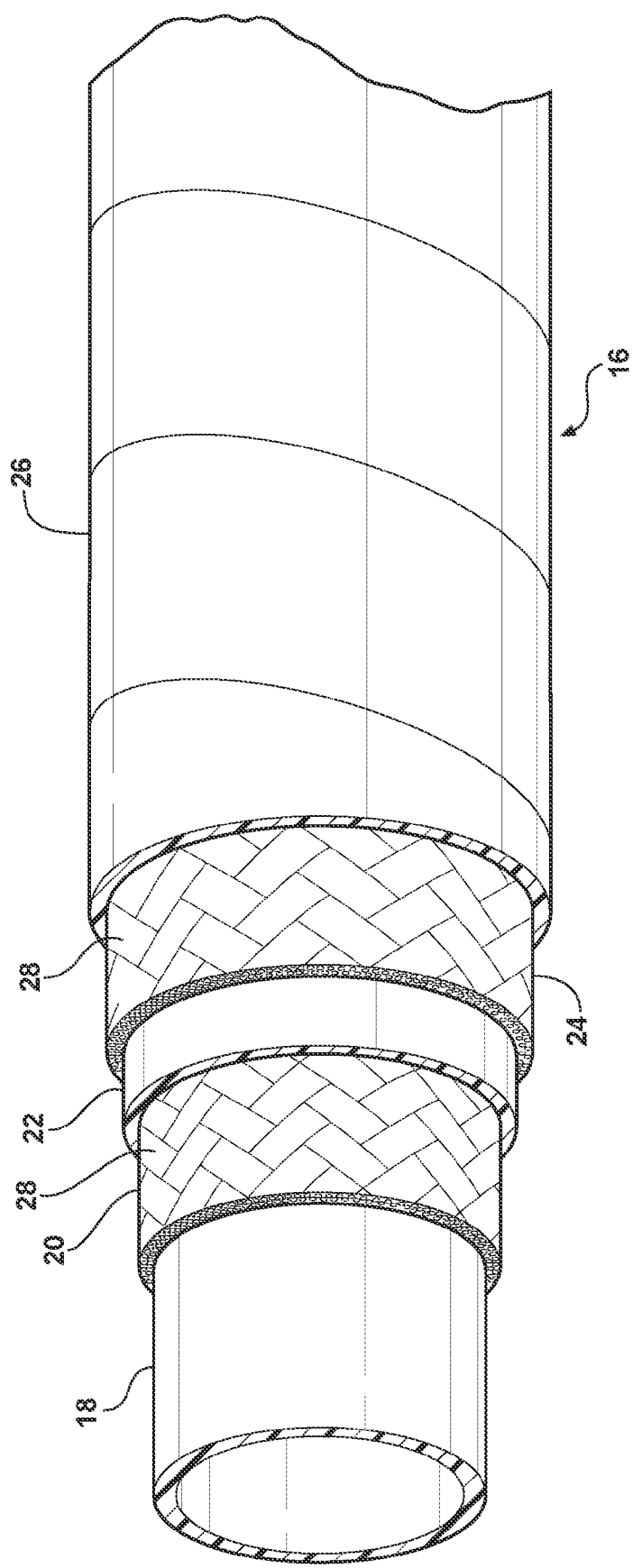
FIG. 2 is a perspective view, partially cut away, illustrating an exemplary hose employing a braided conductive layer that is suitable for use with the hose assembly of FIG. 1.
Figure 3:
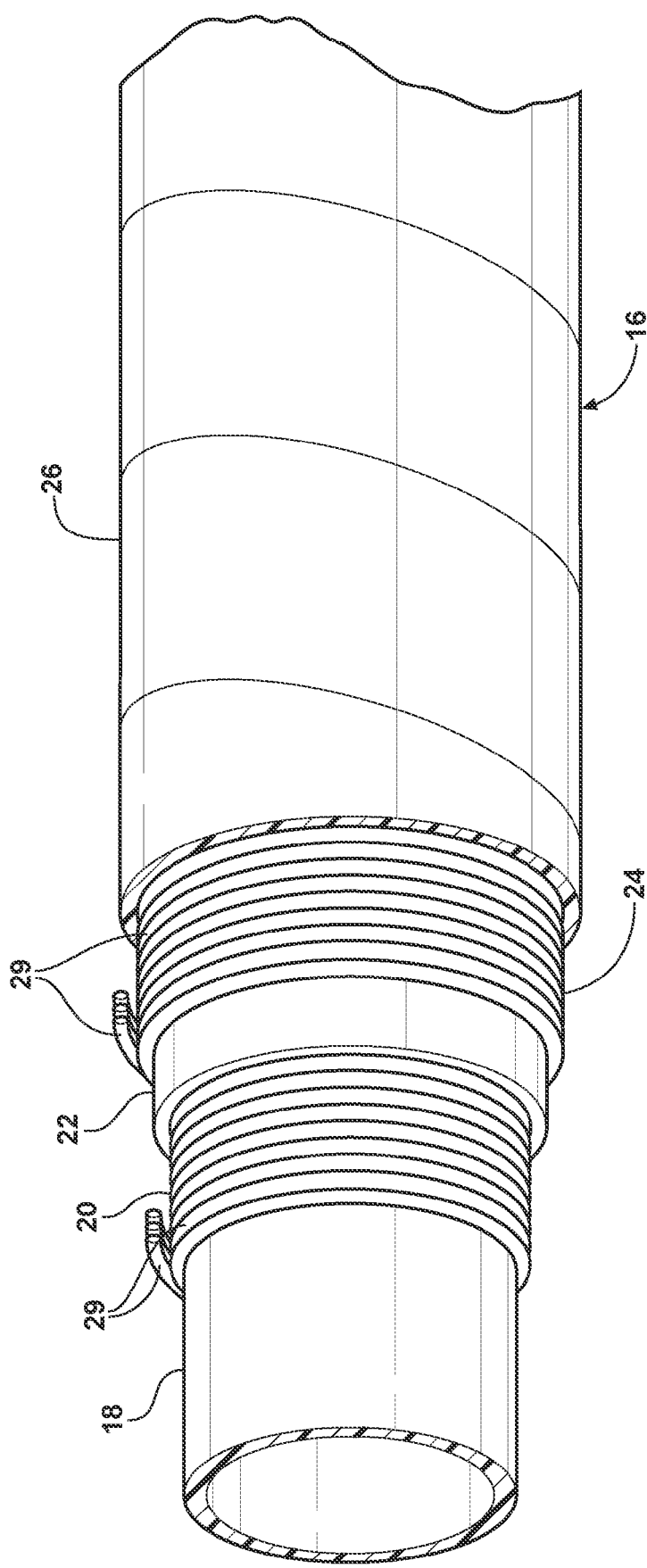
FIG. 3 is a perspective view, partially cut away, illustrating an exemplary hose employing a spiral wire conducting layer that is suitable for use with the hose assembly of FIG. 1.

Referring now to FIGS. 2 and 3, the first and second conductive layers 20, 24 may include, for example, an electrically conductive braided reinforcement material 28, such as shown in FIG. 2, or alternating layers of electrically conductive spiral reinforcement material 29, such as shown in FIG. 3. The braided reinforcement material 28 may include a single layer or may include multiple layers. Although a two-wire spiral reinforcement arrangement is depicted in FIG. 3, it shall also be appreciated that other configurations, such as four and six wire arrangements, may also be utilized.

The first and second conductive layers 20, 24 may each have the same configuration, or each layer 20, 24 may be configured differently. For example, the first and second conductive layers 20, 24 may each include the braided reinforcement material 28 shown in FIG. 2, or one of the first and second conductive layers 20, 24 may include the braided reinforcement material 28 while the other of the first and second conductive layers 20, 24 may include the spiral reinforcement material 29 shown in FIG. 3. Additionally, the first and second conductive layers 20, 24 may include a single ply or multiple plies of the reinforcement material 28, 29. The first and second conductive layers 20, 24 may include metal wire, natural or synthetic fibers and textiles, and/or other reinforcement materials, provided the selected materials are electrically conductive.

Referring again to FIG. 1, the hose assembly 12 may include a nipple 32, which engages the inside of the hose 16, and a socket 34, which engages the outside of the hose 16. The nipple 32 and/or the socket may be configured to fluidly couple the hose 16 to another component (not shown). The nipple 32 includes an elongated cylindrical end portion 36 that engages the inner tube 18 of the hose 16. A cylindrically shaped end portion 38 of the socket 34 engages the outer cover 26 of the hose 16. The socket 34 and nipple 32 may be constructed from an electrically conductive material, as known to those skilled in the art.

The socket 34 and nipple 32 can be secured to the hose 16 by crimping the end portion 38 of the socket 34 overlaying the hose 16. The crimping process deforms the end portion 38 of the socket 34, thereby compressing the hose 16 between the nipple 32 and the socket 34. In the subject embodiment, the portions of the nipple 32 and the socket 34 that engage the hose 16 include a series of serrations 39 that at least partially embed into the relatively softer hose 16 material when the socket 34 is crimped to help secure the socket 34 and the nipple 32 to the hose 16. The serrations 39 may be configured to prevent the serrations 39 from penetrating the inner tube 18 and outer cover 26 to contact the first and second conductive layers 20, 24.

In the subject embodiment, the socket 34 includes an inwardly extending circumferential lug 40 positioned near a deformable end 42 of the socket 34 adjacent a hose end 44 of the hose 16. The lug 40 engages a corresponding circumferential slot 46 formed in the nipple 32 for securing the socket 34 to the nipple 32. The deformable end 42 of the socket 34 having the lug 40 is initially formed larger than the nipple 32 to enable the socket 34 to be assembled onto the nipple 32. During the assembly process the deformable end 42 of the socket 34 is crimped, which deforms the socket 34 and forces the lug 40 into engagement with a corresponding slot 46 defined in the nipple 32. The socket 34 can be electrically insulated from the nipple 32 by positioning an electrically insulating collar 48 between the socket 34 and nipple 32 at the point the lug 40 engages the slot 46.

The hose assembly 12 may also include a nut 50 that is attached to the nipple 32 and/or the socket 34. The nut 50 is configured to secure the hose assembly 12 to another component (not shown).

The first conductive layer 20 may be configured to extend beyond an end of the inner tube of the hose 16. The first conductive layer 20 may engage the nipple 32 to create an electrical connection between the nipple 32 and the first conductive layer 20. Similarly, the second conductive layer 24 may be configured to extend beyond an end of the outer cover 26 of the hose 16. The second conductive layer 24 may engage the socket 34 to create an electrical connection between the socket 34 and the second conductive layer 24.

To help prevent the portions of the first and second conductive layers 20, 24 that extend beyond the hose end 44 of the hose 16 from contacting one another, an electrically insulating spacer 52 may be positioned between the exposed ends of the first and second conductive layers 20, 24. The spacer 52 may be integrally formed as part of the collar 48 that is used to electrically insulate the socket 34 from the nipple 32. The spacer 52 may also be formed by extending the intermediate layer 22 of the hose 16 beyond an end of the inner tube 18 and outer cover 26. Alternatively, the spacer 52 may also be configured as a standalone component separate from the collar 48 and the intermediate layer 22 of the hose 16.

The fault detector 14 may have any of a variety of configurations. An exemplary fault detector 14 was described in U.S. patent application Ser. No. 12/499,477, filed Jul. 8, 2009, which is hereby incorporated by reference in its entirety.

Figure 5:
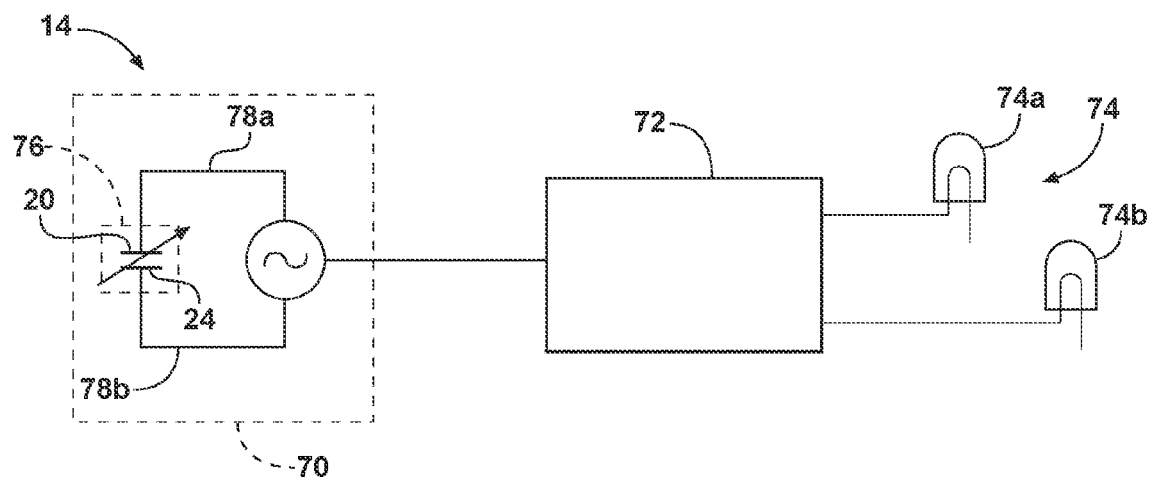
FIG. 5 is an exemplary schematic representation of a fault detector suitable for use with the hose assembly of FIG. 1.

Referring now to FIG. 5, an exemplary schematic representation of the fault detector 14 is shown. The fault detector 14 of the hose fault detection system 10 is used to monitor the structural integrity of the hose 16. In the subject embodiment, the fault detector 14 is configured to cause a visual notification signal to be generated on the hose 16 when the structural integrity of the hose 16 is compromised.

There are a wide variety of mechanisms by which the structural integrity of the hose 16 may be compromised. A hose 16 may be a hydraulic hose that is subjected to cyclic pressure changes that may result in a progressive fatigue induced degeneration of one or more of the layers 20, 24 within the hose 16, which typically precedes a complete failure of the hose 16. For purposes of discussion, a complete failure of the hose 16 occurs when an opening develops in the wall of the hose 16 that allows fluid to escape from the hose 16. The ability to detect degeneration occurring within the hose 16 may provide an opportunity to remove the hose 16 from service prior to a complete failure.

In the subject embodiment, degeneration of the hose 16 produces a corresponding detectable change in the electrical characteristic between the first and second conductive layers 20, 24. In one embodiment, the electrical characteristic is capacitance. In another embodiment, the electrical characteristic is resistance. In yet another embodiment, the electrical characteristic is impedance.

When a change in the electrical characteristic is detected, an operator is forewarned of an impending hose 16 failure. For example, if the intermediate layer 22 of the hose 16 were to develop a tear that results in the first conductive layer 20 electrically contacting the second conductive layer 24, such as shown in FIG. 5, this contact will result in a change in the electrical characteristic of the hose assembly 12 that can be detected by the fault detector 14. It may also be possible that one of the conductive layers 20, 24 could begin to fray. This may be characterized by the breakage of individual wires in instances where the conductive layer 20, 24 is constructed from a braided reinforcement material 28, such as shown in FIG. 2. In one embodiment, the frayed wires may pierce the intermediate layer 22 and contact the opposing conductive layer 20, 24, resulting in a change in the electrical characteristic of the hose assembly 12. In another embodiment, when the wires begin to fray, the change in the physical relationship between the first and second conductive layers 20, 24 results in a change in the electrical characteristic that is detected by the fault detector 14. More specifically, the electrical resistance between the first and second conductive layer 20, 24 may decrease to a low level.

Figure 4A:
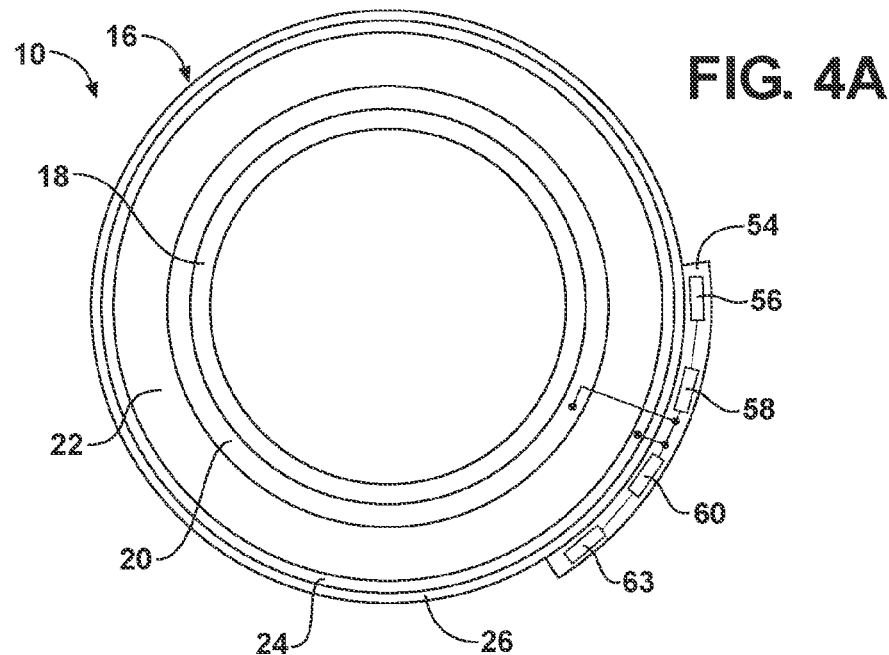
FIG. 4A is a schematic cross-sectional end view of the hose assembly of FIG. 1 illustrating the hose having a microcontroller device attached to conductive layers of the hose.
Figure 4C:
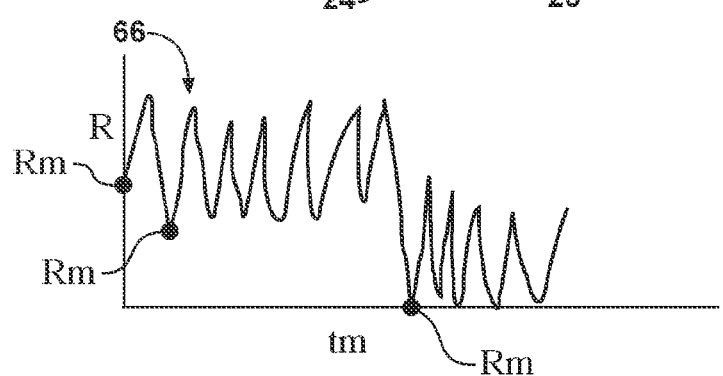
FIG. 4C is a schematic graphical representation of the microcontroller device of FIG. 1 monitoring electrical resistance values over time.
Figure 4D:
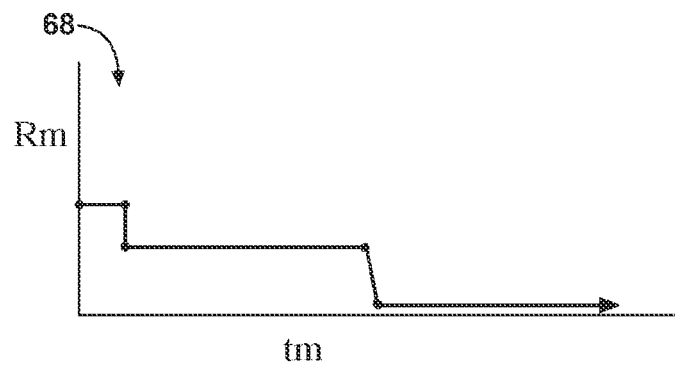
FIG. 4D is a schematic graphical representation of minimum electrical resistance values over time that are stored in the memory of the microcontroller of FIG. 1.

Referring to FIGS. 4A-4D, a microcontroller device 54 may be used to process the electrical resistance and store a relative minimum electrical resistance Rm over a given period of time tm. The microcontroller device 54 is operatively attached to the first and second conductive layers 20, 24 of the hose 16. Referring specifically to FIG. 4A, the microcontroller device 54 may be affixed to the outer layer 26 of the hose 16. It should be appreciated that the microcontroller device 54 may be operatively attached to the first and second conductive layers 20, 24 in any configuration known to those skilled in the art. The microcontroller device 54 includes a sensor 56, a signal conditioner 58, and a memory 60 and processing unit 63 with an analog to digital convertor 61. The sensor 56 is configured to continuously sense the electrical resistance between the first and second conductive layers 20, 24. The signal conditioner 58 is of the type known to those skilled in the art that continuously converts the electrical resistance read by the sensor 56. The processing unit 63 is configured to convert the conditioned electrical resistance from an analog signal to a digital signal. Referring to FIG. 4B, the processing unit 63 of the microcontroller device 54 includes an algorithm 62. The algorithm 62 is initialized by clearing a timer and capturing an associated time that the timer was cleared, as indicated at 100. Once the algorithm 62 is initialized 100, the algorithm 62 sleeps and waits for an event, as indicated at 102. The event may be when the sampling time tm has elapsed, as indicated at 104. When the sampling time tm has elapsed, as indicated at 104, a resistance value R from the hose 16 is read, as indicated at 106. If the resistance value R is not lower than a previously read or a minimum resistance value Rm, nothing further happens, as indicated at 108, and the processing unit 63 continues to sleep and wait for the next event 102. If the resistance value is lower than a previously read resistance, the sampling time tm and the corresponding minimum resistance value Rm are recorded in the memory 60, as indicated at 110, and the processing unit 63 continues to sleep and wait for the next event 102. As the new minimum resistance values Rm are recorded in the memory 60, the minimum resistance values Rm and the corresponding sampling time tm may be read from the memory 60, as indicated at 112, for use by the operator. Likewise, it may be desired to intermittently reset the timer and record the corresponding time tm of the reset in the memory 60, as indicated at 114. Therefore, referring to FIG. 4C, the digital electrical resistance is stored in the memory 60 whenever the electrical resistance is determined to be at a new minimum value, as indicated at 66. The changes in the minimum resistance values Rm of the electrical resistance R may be plotted over time tm, as shown in FIG. 4D. Referring to FIG. 4D, the processing unit 63 is also configured to monitor the electrical resistance and store the minimum electrical resistance Rm over time tm in the memory 60, as indicated at 68.

In another embodiment, shown in FIGS. 1 and 5, a change in the physical relationship between the two conductive layers 20, 24, such as may occur due to swelling of the hose 16 that may be caused by fluid entering one or more of the hose layers 20, 22, 24, 26 through an interior fault in the hose 16, may produce a corresponding change in the electrical characteristic. In the subject embodiment, upon detecting a change in the monitored electrical characteristic, the fault detector 14 provides a visual notification to the operator that signals the presence of a fault within the hose assembly 12.

In the embodiment of FIG. 5, the electrical characteristic being monitored is electrical impedance between the first conducting layer 20 and the second conducting layer 24. In the subject embodiment, the fault detector 14 includes an oscillator 70 and a comparator 72 in electrical communication with the oscillator 70. In the subject embodiment, the fault detector 14 further includes at least one visual indicator 74, which is disposed directly on the hose assembly 12, in electrical communication with the comparator 72.

Referring again to FIG. 5, the oscillator 70 is in electrical communication with a power source. In one embodiment, the power source is a direct current (DC) power source that is found on an off-highway vehicle employing the use of the hose fault detection system 10. The oscillator 70 is configured to convert direct current from the power source to alternating current (AC).

The oscillator 70 includes a circuit having active and passive devices, such as an operational amplifier, capacitors, resistors, etc. In the depicted embodiment of FIG. 5, the first and second conductive layers 20, 24 of the hose assembly 12 form a variable impedance 76 which is in electrical communication with the oscillator 70 through first and second electrical leads 78a, 78b. In one embodiment, the first electrical lead 78a is directly connected to the first conductive layer 20 while the second electrical lead 78b is directly connected to the second conductive layer 24. In another embodiment, the first electrical lead 78a is directly connected to the nipple 32, which is in electrical communication with the first conductive layer 20 while the second electrical lead 78b is directly connected to the socket 34 which is in electrical communication with the second conductive layer 24.

Figure 6:
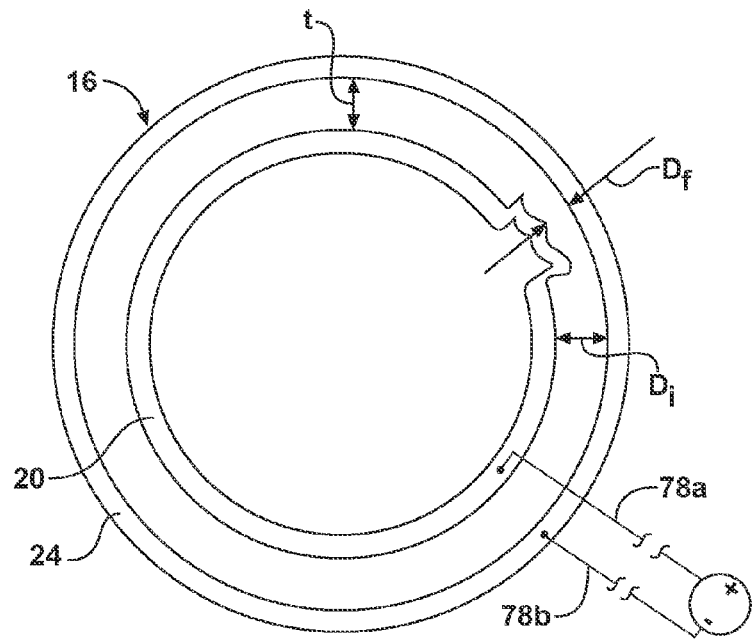
FIG. 6 is a schematic cross-sectional end view of the hose assembly of FIG. 1 illustrating the hose having an initial distance between the conductive layers and a deformed distance between the conducting layers.

As previously discussed, the oscillator 70 outputs an output signal having a frequency. In the subject embodiment, the oscillator 70 outputs a sinusoidal-shaped signal. Changes in the electrical characteristic of the hose assembly 12 affect the output signal of the oscillator 70. For example, referring to FIG. 6, as an initial distance Di between the first and second conducting layers 20, 24 changes to a deformed distance Df, the electrical characteristic of the hose assembly 12 also changes. As the electrical characteristic of the hose assembly 12 changes, the frequency of the output signal changes.

Referring again to FIG. 5, the oscillator 70 is in electrical communication with the comparator 72. In the subject embodiment, the comparator 72 detects changes in the output signal from the oscillator 70 and thus detects changes in the electrical characteristic of the hose assembly 12. The comparator 72 includes a microprocessor 80 configured for performing various calculations and manipulations of the received electrical characteristic.

Referring again to FIG. 5, at least one visual indicator 74 is in electrical communication with the comparator 72. The visual indicator 74 provides notification to the operator that the structural integrity of the hose assembly 12 has been compromised even though the hose assembly 12 may still be operational. This notification prior to failure of the hose assembly 12 allows the operator to replace the hose assembly 12 before the hose 16 develops a leak. The visual indicator 74 allows operators to identify hoses 16 having decreased structural integrity without having to remove the hoses 16 from the vehicle. In the subject embodiment, the visual indicator 74 is a light, such as a light-emitting diode (LED). The use of the visual indicator 74 may be incorporated into a time or usage based maintenance schedule that requires the operators to proactively obtain and interpret the reading from the visual indicator 74.

In one embodiment, the light intensity of the visual indicator 74 corresponds to a thickness t of the intermediate layer 22 of the hose 16. For example, the fault detector 14 can be configured such that as the thickness t of the intermediate layer 22 of the hose 16 decreases, the light intensity of the visual indicator 74 increases.

Referring again to FIG. 5, the fault detector 14 may include a first visual indicator 74A and a second visual indicator 74B. The comparator 72 illuminates the first visual indicator 74A to provide visual notification to the operator that the structural integrity of the hose assembly 12 is capable of operating at rated conditions for the hose assembly 12. As the hose assembly 12 begins to degrade (e.g., the thickness t of the intermediate layer 22 begins to decrease), the comparator 72 illuminates the second visual indicator 74B to notify the operator of an impending failure of the hose assembly 12.

In one embodiment, the microprocessor 80 compares the frequency of the output signal from the oscillator 70 resulting from the electrical impedance between the first and second conducting layers 20, 24 to a threshold value. The frequency of the output signal from the oscillator 70 changes in response to changes in the initial distance Di between the first conducting layer 20 and the second conducting layer 24 to the deformed distance Df. For example, as the initial distance Di between the first and second conducting layers 20, 24 decreases to the deformed distance Df, the electrical impedance between the first and second conducting layers 20, 24 decreases, thus changing the frequency of the output signal from the oscillator 70.

In one embodiment, the threshold value is a preprogrammed value that serves as a limit for the electrical characteristic. In another embodiment, the threshold value is a value that is determined during the initial operation of the hose assembly 12. In another embodiment, the threshold value is a range of values that serve as upper and lower limits.

In one embodiment, and by way of example only, if the frequency of the output signal is about equal to the threshold value for frequency or within the range of values for frequency, the initial distance Di between the first and second conducting layers 20, 24 is unchanged. In this situation, the comparator 72 illuminates the first visual indicator 74A, which notifies the operator that the hose assembly 12 is capable of operating at rated pressures. If, however, the frequency of the output signal is below the threshold value for frequency or outside of the range of values for frequency, the initial distance Di between the first and second conducting layers 20, 24 has decreased to the deformed distance Df. In this situation, the comparator 72 illuminates the second visual indicator 74B, which notifies the operator that the structural integrity of the hose assembly 12 has been compromised.

Figure 7:
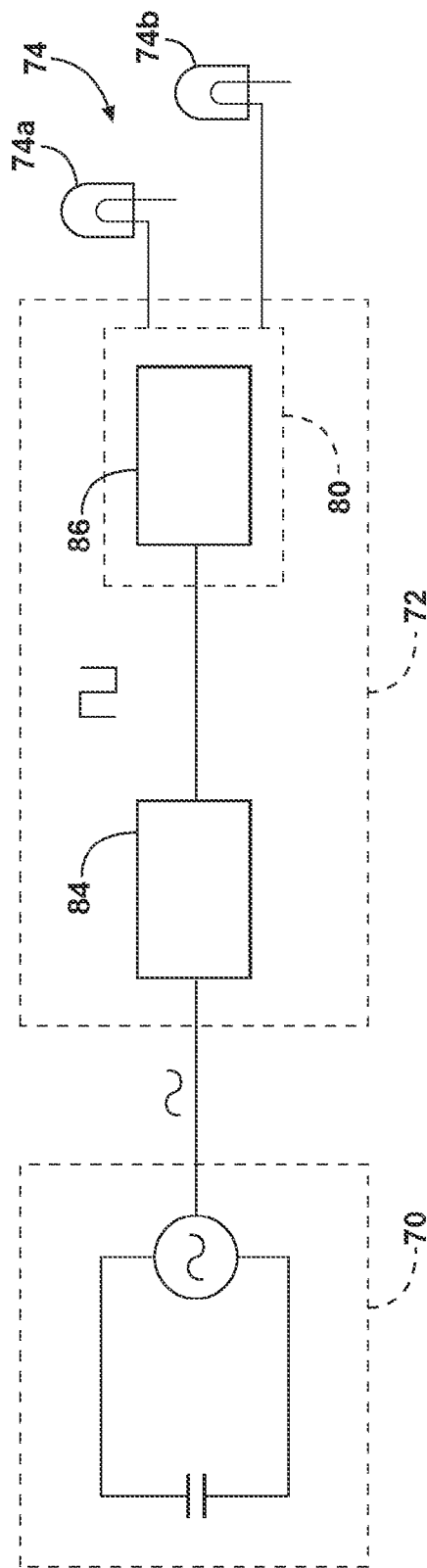
FIG. 7 is an exemplary schematic representation of a comparator suitable for use with the fault detector of FIG. 1.

Referring now to FIG. 7, a schematic representation of the comparator 72 is shown. In the subject embodiment, the comparator 72 includes a wave shaping function 84 and a processing function 86. The wave shaping function 84 converts the sinusoidal-shaped output signal from the oscillator 70 to a square-shaped signal. The processing function 86 receives the square-shaped signal and detects changes in frequency of the square-shaped wave or an absence of the square-shaped wave. Depending on the signal received from the wave shaping function 84, the processing function 86 illuminates either the first or second visual indicators 74A, 74B.

Figure 8:
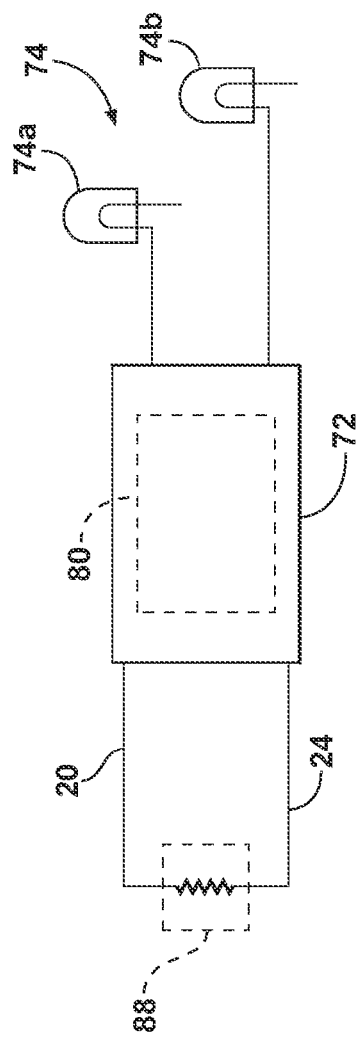
FIG. 8 is an alternative exemplary schematic representation of a fault detector suitable for use with the hose assembly of FIG. 1.

Referring now to FIG. 8, an alternate exemplary schematic representation of the fault detector 14 is shown. In the subject embodiment, the fault detector 14 includes a variable resistor 88, the comparator 72, which is in electrical communication with the variable resistor 88, and at least one visual indicator 74, which is in electrical communication with the comparator 72.

In the subject embodiment, the electrical characteristic of the hose assembly 12 being monitored is the electrical resistance between the first conducting layer 20 and the second conducting layer 24. This electrical resistance is variable. This means that as the initial distance Di between the first and second conducting layers 20, 24 changes to the deformed distance Df, the electrical resistance also changes. For example, as the initial distance Di between the first conducting layer 20 and the second conducting layer 24 decreases to the deformed distance Df, the electrical resistance between the first and second conducting layers 20, 24 also decreases.

In one embodiment, shown in FIG. 7, the microprocessor 80 of the comparator 72 compares the electrical resistance between the first and second conducting layers 20, 24 to a threshold value. In one embodiment, the threshold value is a preprogrammed value that serves as a lower limit for the electrical resistance. If the electrical resistance is less than the threshold value, the hose assembly 12 is interpreted as having a failing health status and the hose assembly 12 should be removed from operation. This is because an electrical resistance below the threshold reading may be consistent with a hose 16 that contains internal structure faults such that the hose assembly 12 may be close to failing. Likewise, if the electrical resistance is equal to, or greater than the threshold value, the hose assembly 12 is interpreted as having a passing health status and the hose assembly 12 should remain in operation. In another embodiment, and by way of example only, the threshold value is about 10 milli-Ohms (mΩ). It should be appreciated that the threshold value may be any suitable value known to those skilled in the art.

In one embodiment, and by way of example only, if the electrical resistance is greater than or equal to the threshold value, the initial distance Di between the first and second conducting layers 20, 24 is unchanged. If, however, the electrical resistance is less than the threshold value, the initial distance Di between the first and second conducting layers 20, 24 has decreased to the deformed distance Df. In this situation, the comparator 72 illuminates the visual indicator 74, which notifies the operator that the structural integrity of the hose assembly 12 has been compromised.

Figure 9:
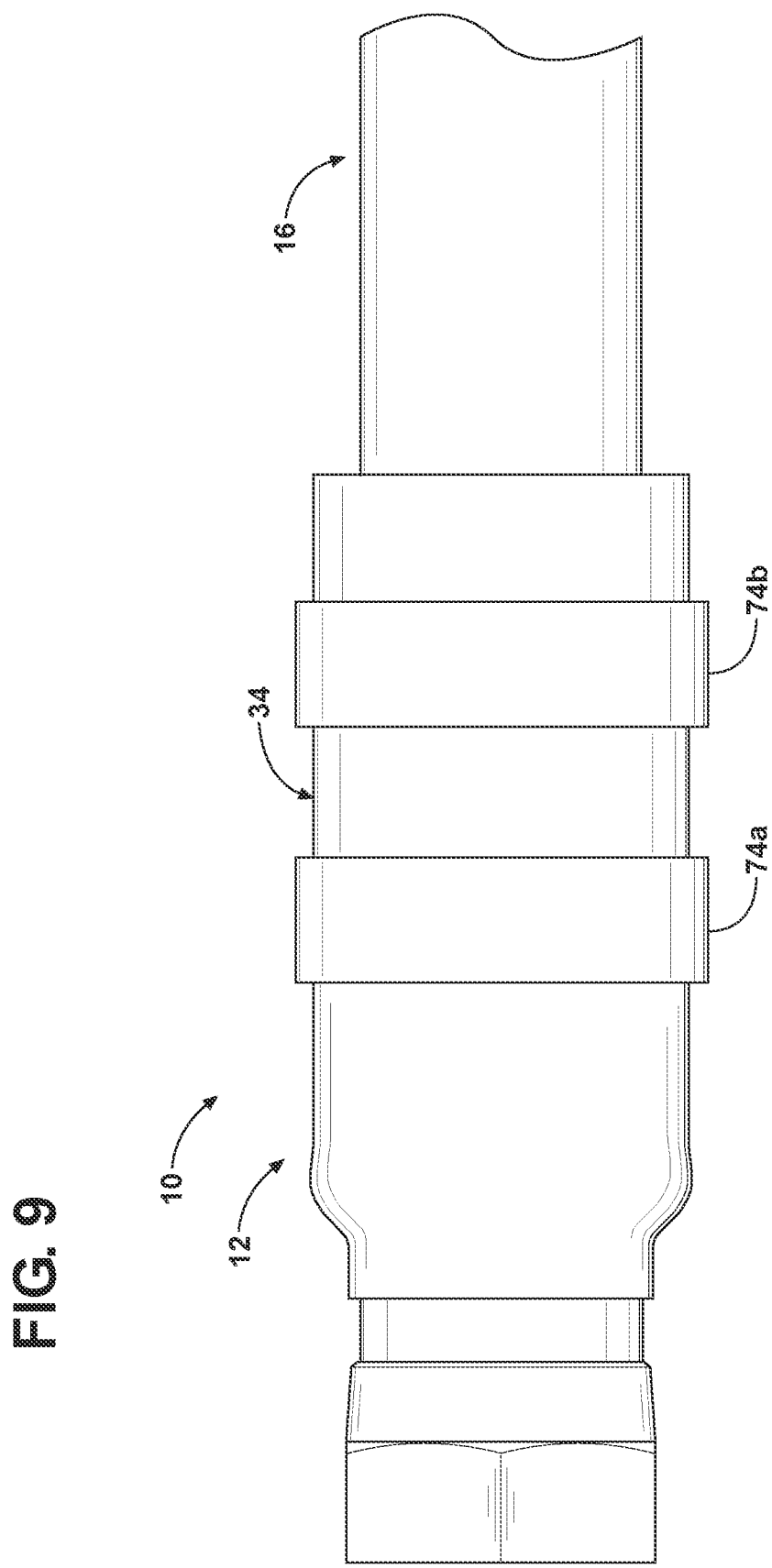
FIG. 9 is a side view of an alternate embodiment of the hose assembly of FIG. 1.

In another embodiment, shown in FIGS. 5 and 7-9, the fault detector 14 includes the first visual indicator 74A and the second visual indicator 74B. Referring specifically to FIG. 9, the first visual indicator 74A is disposed directly on the hose assembly 12 while the second visual indicator 74B is disposed at a location remote from the hose assembly 12. If the electrical resistance of the hose assembly 12 is less than the threshold value, the comparator 72 illuminates the first and second visual indicators 74A, 74B. This arrangement of visual indicators 74 is potentially advantageous as the second visual indicator 74B notifies the operator of the vehicle of an impending failure of a hose assembly 12 while operating the vehicle while the first visual indicator 74A identifies the hose assembly 12 having the decreased structural integrity.

Referring again to FIG. 1, the hose assembly 12 is shown with the visual indicator 74 disposed directly on the hose 16 of the hose assembly 12. In one embodiment, the visual indicator 74 could also be affixed to a sleeve (not shown) that surrounds a portion of the outer cover 26 of the hose 16. In another embodiment, the visual indicator 74 can be embedded in the outer cover 26 of the hose 16.

Referring again to FIG. 9, the visual indicator 74 can be disposed on the socket 34. In one embodiment, the visual indicator 74 extends fully around the socket 34 such that the visual indicator 74 can be viewed from any angle around the socket 34.

Figure 10:
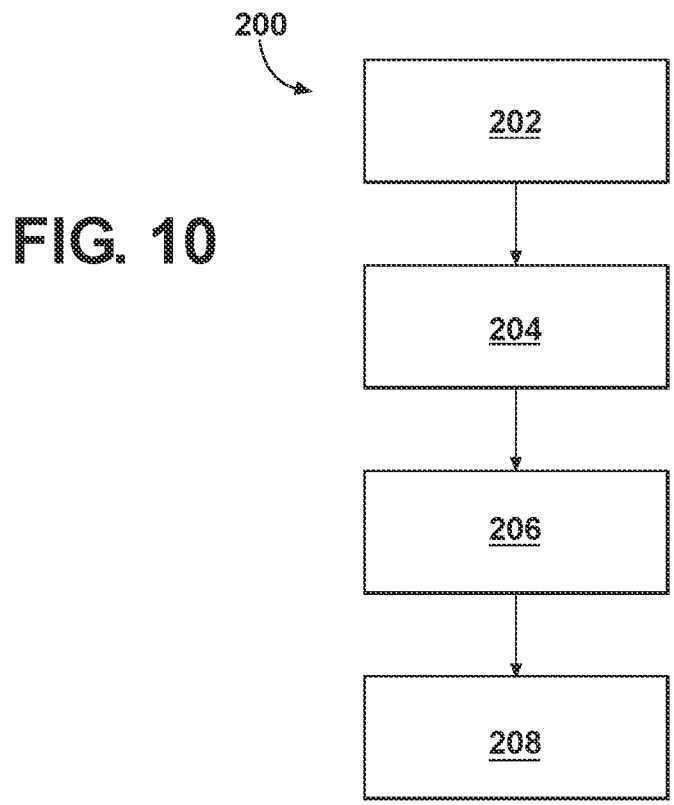
FIG. 10 is a representation of a method for monitoring the structural integrity of the hose assembly of FIG. 1.

Referring now to FIG. 10, a method 200 for monitoring the structural integrity of the hose assembly 12 will be described. In step 202, the hose assembly 12, including the hose 16 having the first and second conductive layers 20, 24, is provided. In the subject embodiment, the hose 16 includes the first conductive layer 20 overlaying at least a portion of the inner tube 18, an intermediate layer 22 overlaying the first conductive layer 20, and the second conductive layer 24 overlaying at least a portion of the intermediate layer 22.

In step 204, an electrical characteristic of the hose assembly 12 is monitored. In one embodiment, the electrical characteristic is capacitance. In another embodiment, the electrical characteristic is resistance.

If the electrical characteristic being monitored is capacitance, a voltage or current is applied to the oscillator 70 of the fault detector 14 prior to step 204. In one embodiment, the voltage or current is continuously applied to the oscillator 70 of the fault detector 14. In another embodiment, the voltage or current is intermittently applied to the oscillator 70 of the fault detector 14. In another embodiment, the voltage or current is applied to the oscillator 70 of the fault detector 14 only when the hose assembly 12 is pressurized.

The monitored electrical characteristic is compared to a threshold value in step 206. In the subject embodiment, the microprocessor 80 performs this comparison. In one embodiment, the threshold value is a value that is preprogrammed. In another embodiment, the threshold value is a value that is determined during the initial operation of the hose assembly 12.

In step 208, the visual indicator 74 is illuminated if the monitored electrical characteristic goes beyond the threshold value. In one embodiment, the visual indicator 74 is illuminated if the monitored electronic characteristic is less than the threshold value. In another embodiment, the visual indicator 74 is illuminated if the monitored electronic characteristic is outside a predetermined range of values.

In an alternate embodiment, the first and second visual indicators 74A, 74B are used to notify the operator of the structural integrity of the hose assembly 12. The first visual indicator 74A is illuminated if the monitored electrical characteristic is greater than or equal to the threshold value or if the monitored electrical characteristic is within a predetermined range of values while a second visual indicator 74B is illuminated if the monitored electrical characteristic is less than the threshold value or if the monitored electrical characteristic is outside the predetermined range of values.

Figure 11:
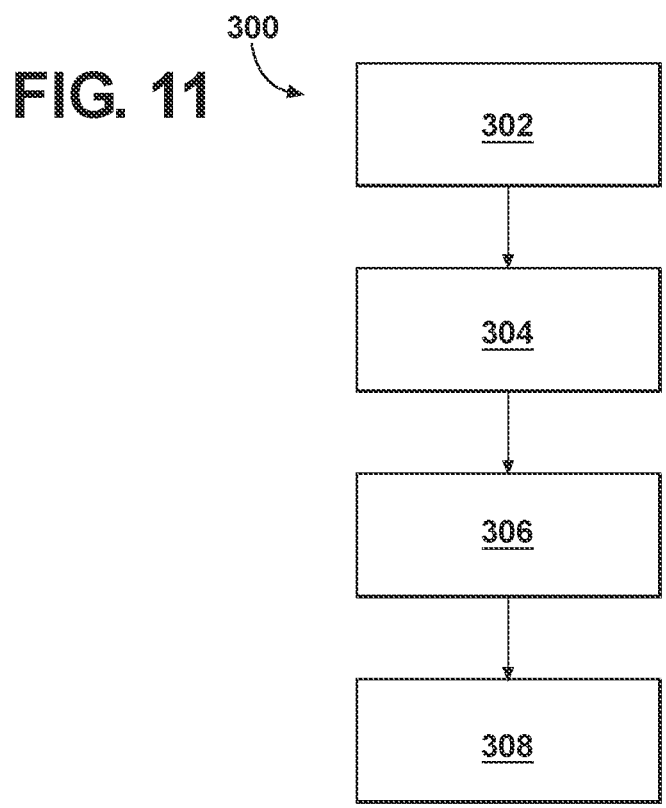
FIG. 11 is a representation of a method for notifying an operator of the structural integrity of the hose assembly of FIG. 1.

Referring now to FIGS. 9 and 11, a method 300 for notifying an operator of the structural integrity of a hose assembly 12 will be described. In step 302, the hose assembly 12 having the first conductive layer 20 overlaying at least a portion of the inner tube 18, an intermediate layer 22 overlaying the first conductive layer 20, and the second conductive layer 24 overlaying at least a portion of the intermediate layer 22 is provided. In one embodiment, the hose assembly 12 includes at least one visual indicator 74 disposed on the hose assembly 12. In another embodiment, the hose assembly 12 includes the first and second visual indicators 74A, 74B disposed on the hose 16. In another embodiment, the hose assembly 12 includes the first and second visual indicators 74A, 74B disposed on the socket 34.

In step 304, the monitored electrical characteristic of the hose assembly 12 is compared to the threshold value. In step 306, the visual indicator 74 is illuminated in response to the monitored electrical characteristic. In one embodiment, the first visual indicator 74A is disposed on the hose assembly 12 (e.g., the hose 16, the socket 34, etc.) and is illuminated only when the electrical characteristic of the hose assembly 16 is greater than or equal to the threshold value or if the electrical characteristic is within a predetermined range of values while the second visual indicator 74B, which is disposed on the hose assembly 12, is illuminated only if the electrical characteristic is less than the threshold value or if the electrical characteristic is outside the predetermined range of values.

In step 308, the intensity of the visual indicator 74 is set based on the difference between the monitored electrical characteristic and the threshold value. In one embodiment, the intensity of the first and second visual indicators 74A, 74B increases as the difference between the monitored electrical characteristic and the threshold value increases. For example, if the monitored electrical characteristic is slightly less than the threshold value, the second visual indicator 74B will be dimly illuminated. If, however, the monitored characteristic is substantially less than the threshold value, the second visual indicator 74B will be brightly illuminated.

Figure 12:
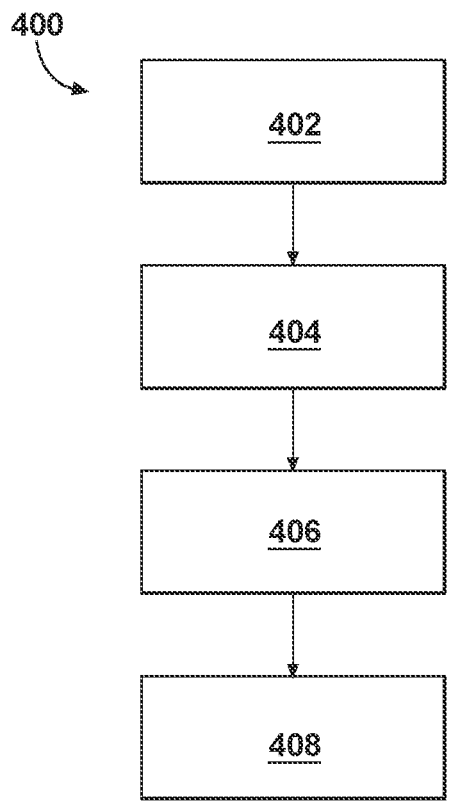
FIG. 12 is an alternate representation of a method for notifying an operator of the structural integrity of the hose assembly of FIG. 1.

Referring now to FIGS. 1 and 12, an alternate method 400 for notifying an operator of the structural integrity of a hose assembly 12 will be described. In step 402, the hose assembly 12 having the first conductive layer 20 overlaying at least a portion of the inner tube 18, an intermediate layer 22 overlaying the first conductive layer 20, and the second conductive layer 24 overlaying at least a portion of the intermediate layer 22 is provided. In one embodiment, the hose assembly 12 includes at least one visual indicator 74 disposed on the hose assembly 12. In another embodiment, the hose assembly 12 includes the first visual indicators 74A disposed directly on the hose assembly 12 while the second visual indicator 74B is disposed in a remote location from the hose assembly 12 such as a cabin of the vehicle (not shown).

In step 404, the monitored electrical characteristic of the hose assembly 12 is compared to the threshold value. In step 406, the first and second visual indicators 74A, 74B are illuminated in response to the monitored electrical characteristic. In one embodiment, the first and second visual indicators 74A, 74B are illuminated when the electrical characteristic of the hose assembly 12 is less than or equal to the threshold value or outside the range of values for the threshold value.

In step 408, the intensity of the first and second visual indicators 74A, 74B is set based on the difference between the monitored electrical characteristic and the threshold value. In one embodiment, the intensity of the first and second visual indicators 74A, 74B increases as the difference between the monitored electrical characteristic and the threshold value increases. For example, if the monitored electrical characteristic is slightly less than the threshold value, the first and second visual indicators 74A, 74B will be dimly illuminated. If, however, the monitored characteristic is substantially less than the threshold value, the first and second visual indicators 74A, 74B will be brightly illuminated.

Figure 13:
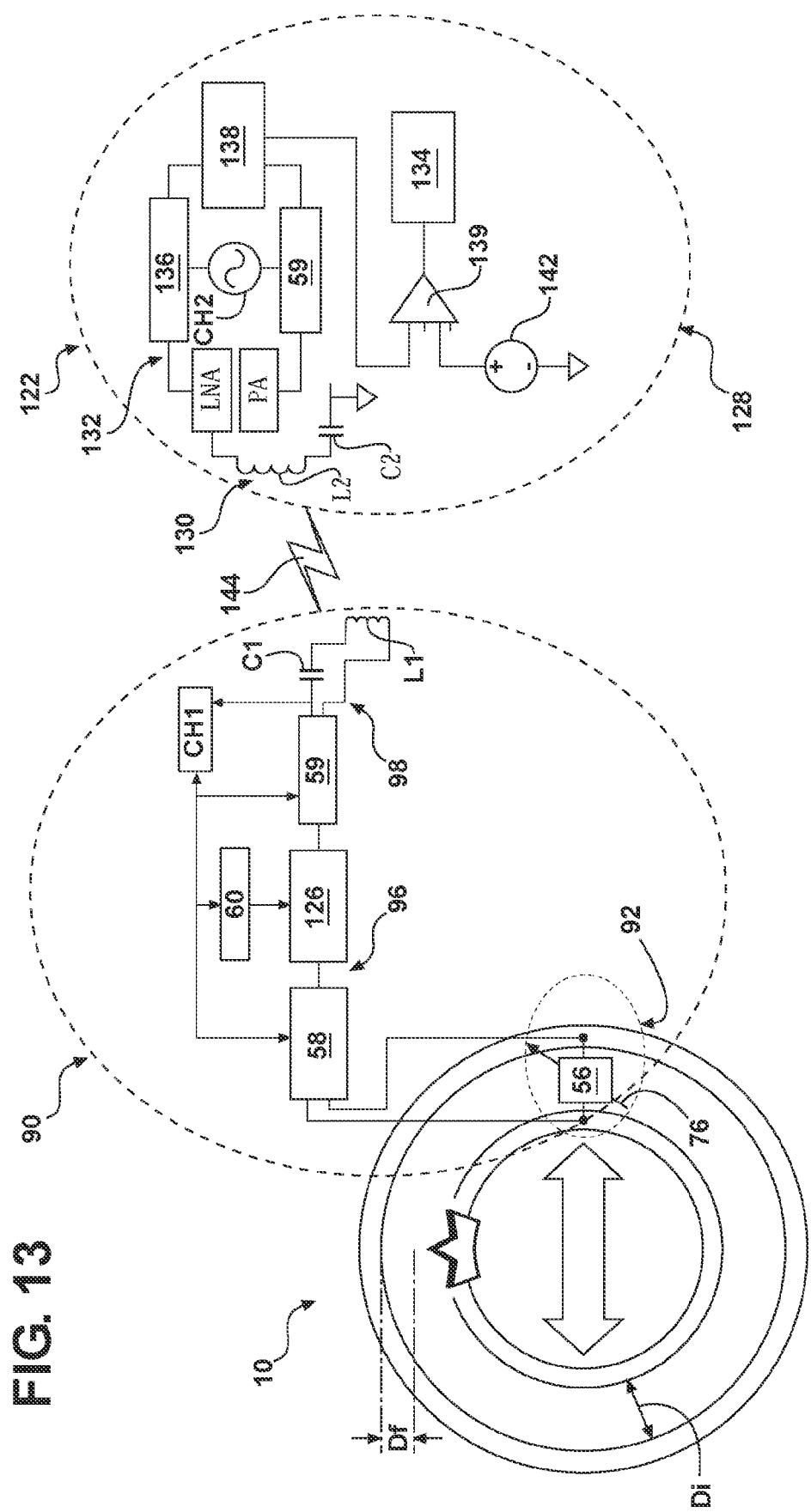
FIG. 13 is a schematic cross-sectional end view of an alternate embodiment of the hose assembly of FIG. 1 illustrating the hose having an RFID system and a reader in operative communication with the RFID system via inductive coupling.

As discussed above, the electrical characteristic of the hose assembly 12 may be monitored using a time or usage based maintenance schedule. In an alternative embodiment, shown in FIGS. 13 and 14, a radio frequency identification (RFID) system 90 is provided with the hose assembly 12. The RFID system 90 includes a first circuit 92 that has an impedance sensor 56, an RFID tag 96, and a first antenna 98. The RFID system 90 is configured to communicate the status of the electrical characteristic of the hose assembly 12 to a mobile scanner ("reader") 122. The reader 122 is configured to be used within a given distance of the hose assembly 12 that is determined by a frequency of communication of the first antenna 98 within the RFID system 90 and the operating environment of the hose assembly 12. The reader 122 may be "near field" or "far field" as known to those skilled in the art. Generally, near field means that the reader 122 communicates with the RFID tag 96 at a closer proximity than if the reader 122 is far field. In this embodiment, the electrical characteristic being monitored is the electrical impedance 76 between the first conducting layer 20 and the second conducting layer 24. Referring specifically to FIG. 13, the RFID tag 96 includes a first power supply CH1, the signal conditioner 58, a digital processing unit 126, the memory 60, and a modulator 59. The first antenna 98 includes a first capacitor C1 operatively connected to a first coil L1. In this embodiment, the first antenna 98 draws power from the first power supply CH1 of the RFID tag 96. The sensor 56 is configured to detect changes of the electrical impedance 76, i.e., "leakage impedance", between the first and second conductive layers 20, 24 that may be related to the fluid pressure within the hose assembly 12 and the deformed distance Df. The RFID tag 96 may be a planar coil, of the type known to those skilled in the art, which is integrated with the socket 34 and/or the hose 16 of the hose assembly 12 to sense the electrical impedance 76 between the first and second conducting layers 20, 24. The sensor 56 operatively connects the first and second conductive layers 20, 24 and the RFID tag 96 of the RFID system 90. Once fatigue of the hose assembly 12 occurs, the electrical impedance 76 between the first and second conducting layers 20, 24 changes permanently. As a result of the permanent change in the electrical impedance 76, the RFID tag 96 is configured to change the load on the first coil L1, resulting in increased amplitude, that can trigger a failure indication in the first circuit 92 of the RFID system 90. Therefore, the output amplitude of the RFID tag 96 is directly related to the electrical impedance 76 of the hose assembly 12.

In the embodiment shown in FIG. 13, the reader 122 includes a second circuit 128 having a second antenna 130, a processing center 132, and a failure indicator 134. The second antenna 130 includes a second capacitor C2 and a second coil L2. The processing center 132 includes a demodulator 136, a modulator 59, a second power supply CH2, a baseband processor 138, a low noise amplifier LNA, a power amplifier PA, a differential amplifier 139, and a DC power supply 142. The second antenna 130 is configured to draw power from the second power supply CH2 of the processing center 132. The differential amplifier 139 is operatively connected to the baseband processor 138, the DC power supply 142, and the failure indicator 134. The failure indicator 134 is configured to indicate to the operator an impending hose 16 failure. It should be appreciated that the reader 122 may be of any other type known to those skilled in the art.

The first circuit 92 of the RFID system 90 and the second circuit 128 of the reader 122 are initially tuned by setting a frequency of the voltage source CH1 to the resonance frequency of the first coil L1 and the first capacitor C1, i.e., a reference frequency. The second voltage source CH2, having the same frequency as the resonance frequency, is tuned to the same phase and amplitude of the first voltage source CH1. The output of the comparator 72 is approximately zero when there is no hose assembly 12 within a detection range of the reader 122. The reader 122 remains tuned as long as the electrical impedance 76 of the hose assembly 12 remains within a normal pre-defined state. The RFID system 90 uses inductive coupling between the first and second coils L1, L2 to transduce signals, as indicated at 144 in FIG. 13.

Figure 14:
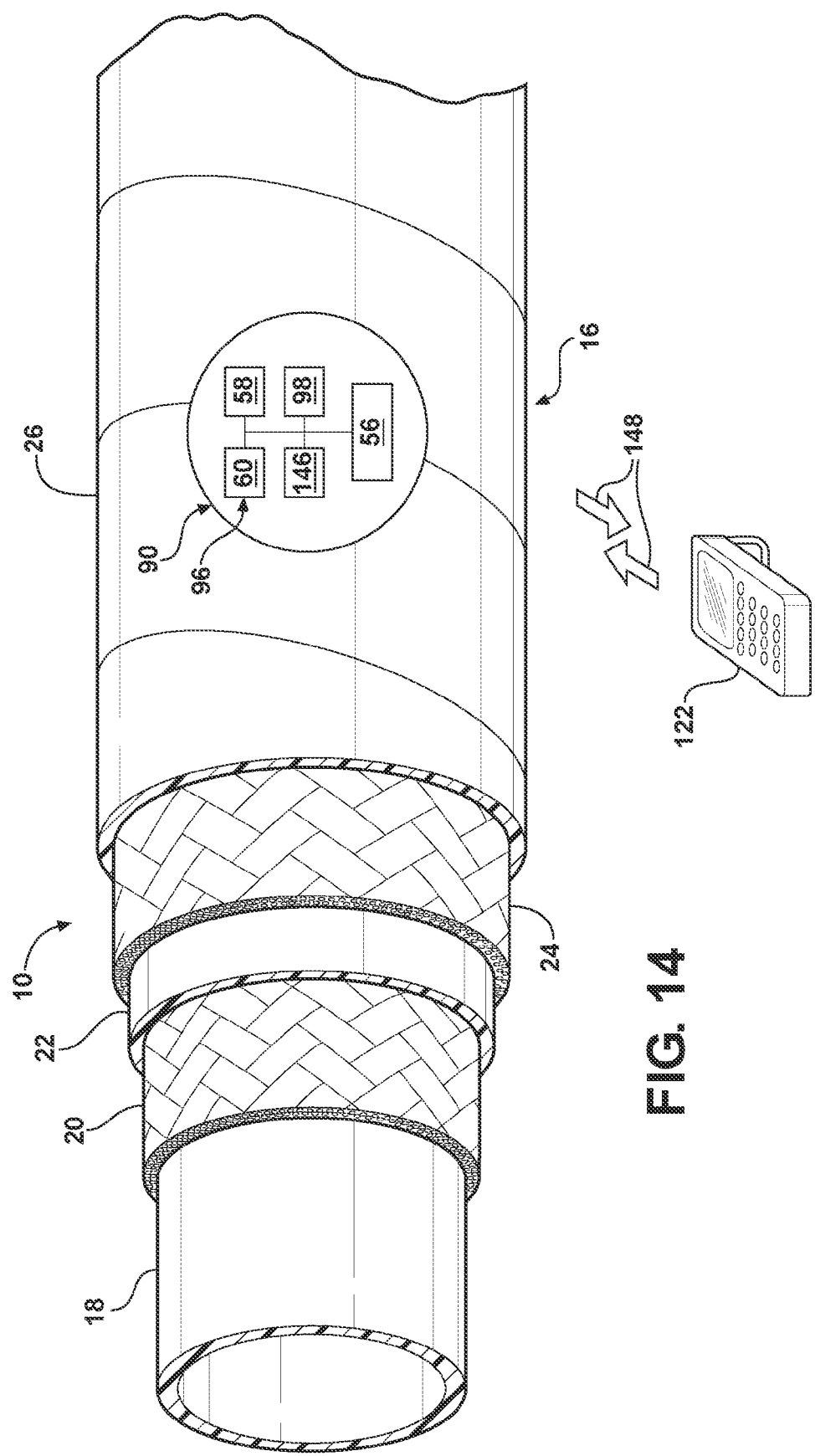
FIG. 14 is a schematic perspective view of another embodiment of the hose assembly of FIG. 1, illustrating the hose having the RFID system and the reader in operative communication with the RFID system via back-scattering.

Referring to FIG. 14, in another embodiment, the hose assembly 12 includes an RFID system 90 having an RFID tag 96 that is integrated with the sensor 56, as known to those skilled in the art. The RFID system 90 includes the sensor 56, the RFID tag 96, and the first antenna 98. In this embodiment, the RFID tag 96 may include the memory 60, the signal conditioner 58, an RF/analog front end 146, and the first antenna 98. The RFID tag 96 may be totally passive, meaning that no battery or other power source is required for operation of the RFID tag 96. When the RFID tag 96 is passive, the RFID tag 96 extracts energy, as indicated at 148, from the incident RFID reader 122. Therefore, a communication distance between the RFID tag 96 and the reader 122 is limited so that the RFID tag 96 can receive enough energy to operate the RFID tag's 96 internal circuitry. The communication between the RFID tag 96 and the reader 122 may be achieved by back-scattering radiation from the reader 122. Additionally, the RFID tag 96 may be configured to upload a history of the electrical impedance 76 and/or pressure associated with the hose assembly 12 to the reader 122. The reader 122 may also be configured to provide an instant status of the health of the hose assembly 12 and alert the operator of any deterioration of the hose assembly 12. In one embodiment, frequencies that are suitable for communication are high frequency of 13.56 MHz and a UHF ban (868 MHz to 930 MHz) frequencies. It should be appreciated that other frequencies known to those skilled in the art may also be used.

Figure 15:
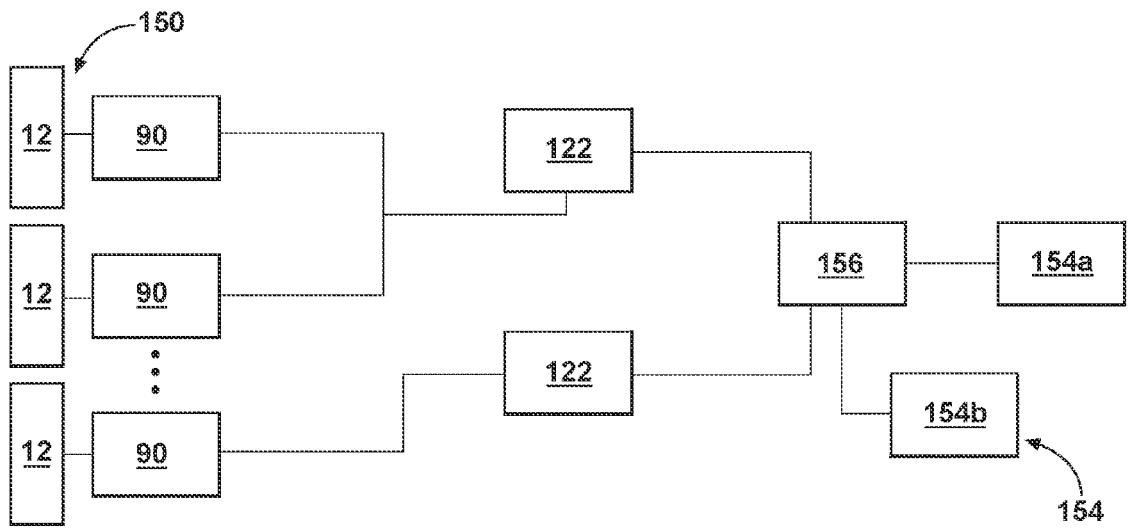
FIG. 15 is a schematic representation of an RFID-based hose failure monitoring system.
Figure 16A:
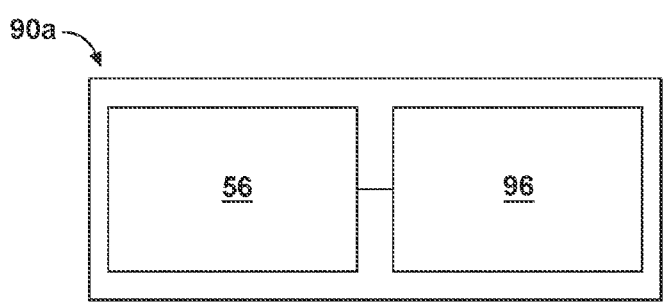
FIG. 16A is a schematic representation of an RFID tag system.
Figure 16B:
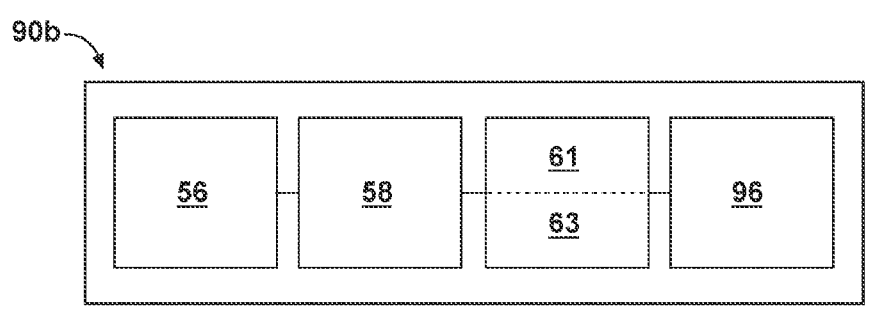
FIG. 16B is a schematic representation of another RFID tag system.

Referring now to FIG. 15, in another embodiment, the RFID tag system 90 may be included as part of a wireless-based hose failure monitoring system 150. In one embodiment, the monitoring system 150 may be an on-line system. The monitoring system 150 may include at least one reader 122, a plurality of RFID tag systems 90 in communication with respective hose assemblies 12, an algorithm 62, and at least one user interface 154. Exemplary RFID tag systems 90 are shown in FIGS. 16A and 16B. Referring to FIG. 16A, the RFID tag system 90*a* includes the sensor 56 operatively connected to the RFID tag 96. In FIG. 16B, the RFID tag system 90*b* includes the sensor 56, the signal conditioner 58, the memory and processing unit 63 and the convertor 61, and the RFID tag 96. In this embodiment, the life sensing hose algorithm 62 may be included within the RFID tag system 90*b*. It should be appreciated, however, that other RFID tag systems 90 known to those skilled in the art may also be used. It should also be appreciated that in this embodiment, the RFID tag system 90 is not limited to being an RFID-based as any other wireless-based system known to those skilled in the art may also be used. It should be appreciated that the RFID tag system 90 may be any other type of wireless tag system 90 known to those skilled in the art.

Referring again to FIG. 15, the readers 122 may be configured as long range readers 122 that are either active or passive. The readers 122 may be located at fixed locations around the RFID tags 96/hose assemblies 12. The reader(s) 122 may be configured to interface with at least one of the RFID tag systems 90 to sense an incumbent hose 16 failure. The detection of the incumbent hose 16 failure may be based off of the electrical impedance 76 measurement between the first and second electrically conductive layers 20, 24. It should be appreciated, however, that other units of measurement known to those skilled in the art may also be used. The algorithm 62 may be configured to be capable of assessing the presence or the absence of a pending and/or actual hose 16 failure. The algorithm 62 may be disposed in a central location that is connected to one or more of the readers 122. The sensed information is read or polled by the respective reader 122, which may process the data received from the RFID tag system 90 and transferred to a central processor 156. The central processor 156 may be disposed in operative communication with each of the readers 122 and a local user interface 154A and/or a remote user interface 154B. The central processor 156 may be responsible for decision making, i.e., deciding whether a respective one of the hoses 16 is about to fail. The decisions from the central processor 156 are transferred in a desired format to user interface via communication links, as known to those skilled in the art. The local user interface 154A may be configured to provide the health status of at least one of the hose assemblies 12 based on information received from the readers 122. The local user interface 154A may be configured to operate at a location that is proximate at least one of the hose assemblies 12. Likewise, the remote user interface 154B may be configured to operate at a location that is remote from the hose assemblies 12 via a remote connection to the central processor 156 to provide the operator with a status of the health of the hose assemblies 12.

Figure 17:
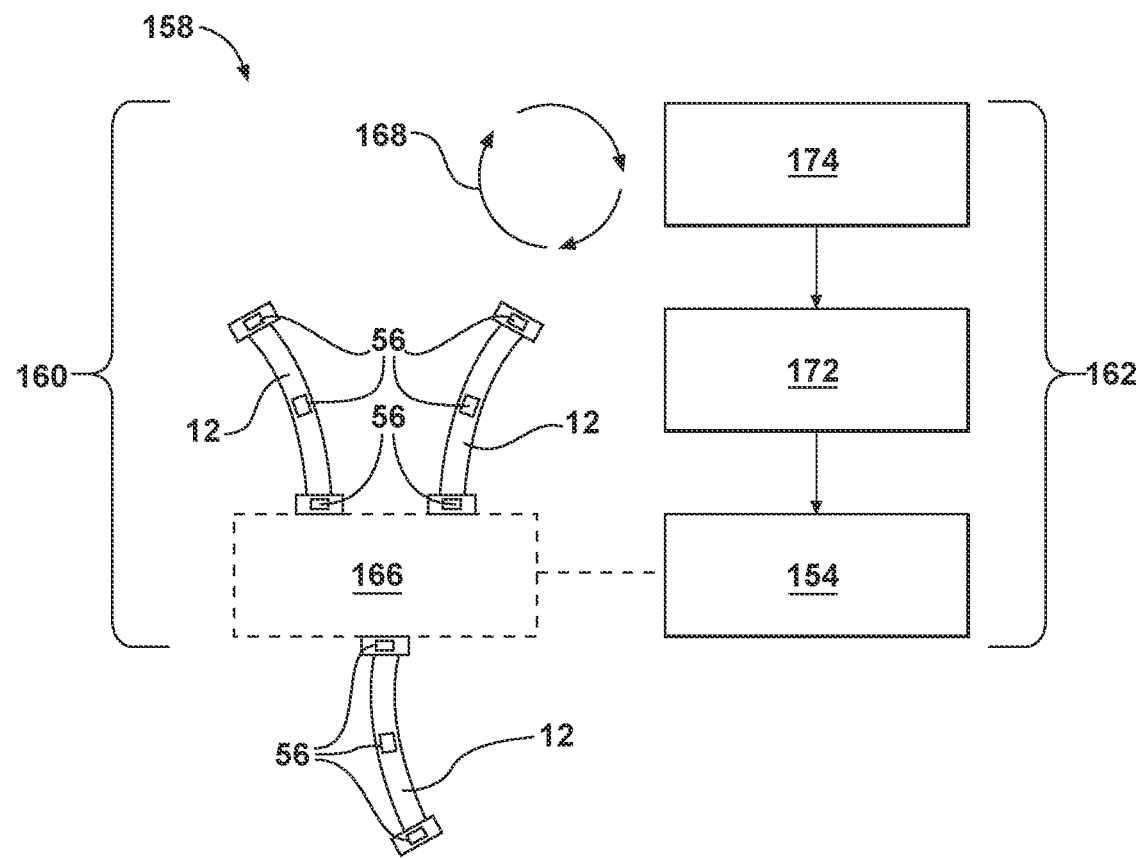
FIG. 17 is a schematic representation of a monitoring and failure detection system for the hose assemblies.

Referring to FIG. 17, a monitoring and failure detection system 158 of the hose assemblies 12 is shown. The monitoring and failure detection system 158 may include at least one sensor node 160 and at least one aggregator node 162. The sensor node 160 may be a plurality of sensors 56 that are installed on the hose 16 and fittings 32, 34, 50 of a machine or device 166 to monitor a characteristics such as electrical, mechanical, chemical, physical, and/or thermal characteristics, e.g., electrical resistance, capacitance, temperature, pressure, etc. In this embodiment, the electrical characteristic being monitored may be monitored as described in the previously described embodiments or as otherwise known to those skilled in the art. Multiple sensor nodes 160 may be used with a single hose assembly 12 to provide redundancy and system fault tolerance. The sensors 56 of the sensor nodes 160 may be attached to the hose assembly 12 such that they may be reused on another hose assembly 12 once the sensor nodes 160 are removed from another hose assembly 12.

The monitored characteristic or data is transmitted to the aggregator node 162 from the respective sensor node 160, as indicated at 168. The aggregator node 162 is configured to analyze the data and provide information, such as an impending failure of the hose assembly 12 and/or the remaining usable life of the hose assembly 12, to a system operator (i.e., a remote control center) 174. The sensor node 160 may provide the information to the aggregator node 162 either periodically and/or based on the occurrence of a specified event. The information is communicated through the aggregator node 162 to the system operator 174 via the user interface 154 to alert the operator to replace the hose assembly 12 before the efficiency of the hose assembly 12 drops or the hose assembly 12 fails entirely. The information may be transmitted via a communication network 172. As employed herein, the term "communication network" 172 shall expressly include, but not be limited by, any local area network (LAN), wide area network (WAN), low-rate wireless personal area network (LR-WPAN), other types of wireless sensor networks, intranet, extranet, global communication network and/or the Internet. As employed herein, the term "wireless" shall expressly include, but not be limited by, RFID, radio frequency (RF), light, visible light, infrared, ultrasound, wireless area networks, IEEE 802.11 (e.g., 802.11a; 802.11b; 802.11g), IEEE 802.15 (e.g., 802.15.1; 802.15.3, 802.15.4), other wireless communication standards, DECT, PWT, pager, PCS, Wi-Fi, Bluetooth™, and cellular As a result, system failures; repair, replacement, and downtime costs; environmental damages; and/or high-pressure fluid leakages may be prevented. Depending on the communication technology and power harvesting method of the monitoring and fault detection system 158, a power source of the sensor node 160 may change, i.e., battery powered, parasitic, hard-wired, etc. When wireless technology is used, the sensor node 160 may have the capability of routing the data of the other sensors 56 to the aggregator node 162, i.e., multi-hop or single hop communication may take place. To save communication bandwidth and energy, the sensor node 160 may also have the capability of aggregating or compressing multiple sensor 56 data as well as employing an efficient sleeping schedule. The aggregator node 162 may be configured to perform computation, communication, and data storage functions. The aggregator node 162 may include the user interface 154 that shows operational parameters of the hose assembly 12, e.g., health status information, remaining usable life of the hose assembly 12, etc. In addition, the aggregator node 162 may have the capability of storing and logging maintenance data, which will provide the operator or maintenance technicians with useful insights about the hose assembly 12. The aggregator node 162 may also be configured to provide the sensor nodes 160 with security and authentication services to protect the system against unauthorized access. Furthermore, the aggregator node 162 may generate diagnostics and prognostics conclusions either by collecting periodic or event-driven data from the sensor nodes 160 or by polling a certain set of sensor nodes 160, i.e., bi-directional communication. The monitoring and failure detection system 158 may be configured as a timely event detection, decision, and acting loop. Depending on the communication environment and application characteristics, the communication architecture of the monitoring and failure detection system may be wired, wireless, or combinations thereof, i.e., hybrid.

Various modifications and alterations of this disclosure will become apparent to those skilled in the art without departing from the scope and spirit of this disclosure, and it should be understood that the scope of this disclosure is not to be unduly limited to the illustrative embodiments set forth herein.

While the best modes for carrying out the invention have been described in detail, those familiar with the art to which this invention relates will recognize various alternative designs and embodiments for practicing the invention within the scope of the appended claims.

The invention claimed is:
1. A hose fault detection system comprising:
a hose assembly including a hose having a first conductive layer and a second conductive layer, wherein the hose assembly has an electrical characteristic; and
a fault detector in electrical communication with the first and second conductive layers;
wherein the fault detector is configured to detect the electrical characteristic;
wherein the fault detector includes a first visual indicator operatively connected to the hose assembly and a second visual indicator;
wherein the first visual indicator is configured to illuminate when the detected electrical characteristic corresponds to the hose assembly being capable of operating; and
wherein the second visual indicator is configured to illuminate when the detected electrical characteristic corresponds to the hose assembly having an impending failure.

2. A hose fault detection system as claimed in claim 1, wherein the second visual indicator is configured to be disposed at a location remote from the hose assembly.

3. A hose fault detection system as claimed in claim 1, wherein the fault detector is a radio frequency identification (RFID) system.

4. A hose fault detection system as claimed in claim 3, wherein the fault detector further includes a reader in operative communication with the RFID system.

5. A hose fault detection system as set forth in claim 4, wherein the reader includes the visual indicator.

6. A hose fault detection system as set forth in claim 5, wherein the RFID system includes a first circuit, an RFID tag, and a first antenna; and
wherein the reader includes a second circuit having a second antenna, a processing center, and a failure indicator.

7. A hose fault detection system as set forth in claim 6, wherein the RFID tag includes a first power supply, a signal conditioner, a digital processing unit, a memory, and a modulator; and
wherein the first antenna includes a first capacitor operatively connected to a first coil.

8. A hose fault detection system as claimed in claim 6, wherein the second antenna includes a second capacitor and a second coil; and
wherein the processing center includes a demodulator, a modulator, a second power supply, a baseband processor, a comparator, and a DC power supply.

9. A hose fault detection system as claimed in claim 1, wherein the fault detector is a microcontroller device having a sensor, a signal conditioner, and a memory and processing unit;
wherein the sensor is configured to continuously sense the electrical characteristic of the hose assembly.

10. A hose fault detection system as claimed in claim 9, wherein the sensor is configured to continuously sense the electrical characteristic of the hose assembly.

* * * * *